United States Patent
Kaspar et al.

(10) Patent No.: US 12,208,144 B2
(45) Date of Patent: Jan. 28, 2025

(54) INTRATHECAL DELIVERY OF RECOMBINANT Adeno-ASSOCIATED VIRUS 9

(71) Applicants: NATIONWIDE CHILDREN'S HOSPITAL, Columbus, OH (US); OHIO STATE INNOVATION FOUNDATION, Columbus, OH (US)

(72) Inventors: Brian K. Kaspar, Columbus, OH (US); Arthur Burghes, Columbus, OH (US); Paul Porensky, Columbus, OH (US)

(73) Assignees: NATIONWIDE CHILDREN'S HOSPITAL, Columbus, OH (US); OHIO STATE INNOVATION FOUNDATION, Columbus, OH (US)

( * ) Notice: Subject to any disclaimer, the term of this patent is extended or adjusted under 35 U.S.C. 154(b) by 790 days.

(21) Appl. No.: 17/206,878

(22) Filed: Mar. 19, 2021

(65) Prior Publication Data
US 2021/0228743 A1 Jul. 29, 2021

Related U.S. Application Data

(63) Continuation of application No. 15/997,433, filed on Jun. 4, 2018, now Pat. No. 11,730,829, which is a continuation of application No. 14/417,823, filed as application No. PCT/US2013/053065 on Jul. 31, 2013, now abandoned.

(60) Provisional application No. 61/678,458, filed on Aug. 1, 2012.

(51) Int. Cl.
| | | |
|---|---|---|
| A61K 48/00 | (2006.01) | |
| A61K 38/17 | (2006.01) | |
| A61K 49/04 | (2006.01) | |
| A61P 25/28 | (2006.01) | |
| C07K 14/47 | (2006.01) | |
| C12N 15/12 | (2006.01) | |
| C12N 15/86 | (2006.01) | |
| C12N 15/864 | (2006.01) | |
| C07H 21/04 | (2006.01) | |

(52) U.S. Cl.
CPC ...... *A61K 48/0075* (2013.01); *A61K 38/1709* (2013.01); *A61K 48/0008* (2013.01); *A61K 49/0438* (2013.01); *C07K 14/47* (2013.01); *C12N 15/86* (2013.01); *A61K 48/00* (2013.01); *C07H 21/04* (2013.01); *C12N 2750/14143* (2013.01)

(58) Field of Classification Search
None
See application file for complete search history.

(56) References Cited

U.S. PATENT DOCUMENTS

| | | |
|---|---|---|
| 5,173,414 A | 12/1992 | Lebkowski et al. |
| 5,658,776 A | 8/1997 | Flotte et al. |
| 5,786,211 A | 7/1998 | Johnson |
| 5,871,982 A | 2/1999 | Wilson et al. |
| 6,258,595 B1 | 7/2001 | Gao et al. |
| 6,566,118 B1 | 5/2003 | Atkinson et al. |
| 6,582,692 B1 | 6/2003 | Podsakoff et al. |
| 6,841,357 B1 | 1/2005 | Vaillancourt et al. |
| 7,198,951 B2 | 4/2007 | Gao et al. |
| 7,906,111 B2 | 3/2011 | Wilson et al. |
| 9,415,121 B2 | 8/2016 | Kaspar et al. |
| 9,725,716 B2 | 8/2017 | Burghes et al. |
| 9,926,574 B2 | 3/2018 | Barkats |
| 10,208,318 B2 | 2/2019 | Barkats |
| 10,301,648 B2 | 5/2019 | Vandenberghe et al. |
| 10,738,326 B2 | 8/2020 | Muramatsu |
| 10,876,134 B2 | 12/2020 | Kielian et al. |
| 11,040,116 B2 | 6/2021 | Kaspar et al. |
| 2002/0192688 A1 | 12/2002 | Yang et al. |
| 2003/0083299 A1 | 5/2003 | Ferguson |
| 2004/0076613 A1 | 4/2004 | Mazarakis et al. |
| 2005/0014262 A1 | 1/2005 | Gao et al. |
| 2005/0053922 A1 | 3/2005 | Schaffer et al. |
| 2007/0036760 A1 | 2/2007 | Wilson et al. |

(Continued)

FOREIGN PATENT DOCUMENTS

| | | | |
|---|---|---|---|
| CN | 101137755 | * | 4/2004 |
| EP | 1620133 A1 | | 2/2006 |

(Continued)

OTHER PUBLICATIONS

Crystal, RG, et al (2004) Clinical protocol Administration of a replication- deficient adeno-associated virus gene transfer vector expressing the human CLN2 cDNA to the brain of children with late infantile neuronal ceroid lipofuscinosis Hum Gene Ther, 2004, 1131-1154.*

(Continued)

*Primary Examiner* — Maria Marvich
(74) *Attorney, Agent, or Firm* — MARSHALL, GERSTEIN & BORUN LLP

(57) ABSTRACT

The present invention relates to Adeno-associated virus type 9 methods and materials useful for intrathecal delivery of polynucleotides. Use of the methods and materials is indicated, for example, for treatment of lower motor neuron diseases such as SMA and ALS as well as Pompe disease and lysosomal storage disorders. It is disclosed that administration of a non-ionic, low-os-molar contrast agent, together with a rAA9 vector for the expression of Survival Motor Neuron protein, improves the survival of SMN mutant mice as compared to the administration of the expression vector alone.

10 Claims, No Drawings

Specification includes a Sequence Listing.

(56) References Cited

U.S. PATENT DOCUMENTS

| | | | |
|---|---|---|---|
| 2007/0280906 A1 | 12/2007 | Petras | |
| 2008/0176799 A1* | 7/2008 | Ferguson | A61K 47/26 514/8.9 |
| 2009/0162332 A1 | 6/2009 | Davidson et al. | |
| 2009/0202490 A1 | 8/2009 | Schaffer et al. | |
| 2010/0130594 A1 | 5/2010 | Barkats | |
| 2010/0240739 A1 | 9/2010 | Barkats | |
| 2012/0177605 A1 | 7/2012 | Kaspar et al. | |
| 2012/0253261 A1 | 10/2012 | Poletto et al. | |
| 2012/0322861 A1* | 12/2012 | Byrne | A61P 9/10 514/44 R |
| 2013/0039888 A1 | 2/2013 | McCarty et al. | |
| 2013/0195800 A1 | 8/2013 | Roeth et al. | |
| 2013/0195801 A1 | 8/2013 | Gao et al. | |
| 2013/0225666 A1 | 8/2013 | Kaspar et al. | |
| 2013/0287736 A1 | 10/2013 | Passini et al. | |
| 2013/0296532 A1 | 11/2013 | Hermens et al. | |
| 2015/0079038 A1 | 3/2015 | Deverman et al. | |
| 2015/0104863 A1 | 4/2015 | Bosch Tubert et al. | |
| 2015/0252384 A1 | 9/2015 | Kaspar et al. | |
| 2016/0038613 A1 | 2/2016 | Kaspar et al. | |
| 2017/0216458 A1 | 8/2017 | Kaspar et al. | |
| 2018/0036431 A1 | 2/2018 | Kaspar et al. | |

FOREIGN PATENT DOCUMENTS

| | | | |
|---|---|---|---|
| JP | 2007-527427 A | 9/2007 | |
| JP | 2007-528424 A | 10/2007 | |
| JP | 2015-525565 A | 9/2015 | |
| WO | WO-95/13365 A1 | 5/1995 | |
| WO | WO-95/13392 A1 | 5/1995 | |
| WO | WO-96/17947 A1 | 6/1996 | |
| WO | WO-97/06243 A1 | 2/1997 | |
| WO | WO-97/08298 A1 | 3/1997 | |
| WO | WO-97/08308 A1 | 3/1997 | |
| WO | WO-97/09441 A2 | 3/1997 | |
| WO | WO-97/21825 A1 | 6/1997 | |
| WO | WO-98/09657 A2 | 3/1998 | |
| WO | WO-99/11764 A2 | 3/1999 | |
| WO | WO-2001/83692 A2 | 11/2001 | |
| WO | WO-2002/081634 A2 | 10/2002 | |
| WO | WO-2004/098648 A1 | 11/2004 | |
| WO | WO-2005/084713 A2 | 9/2005 | |
| WO | WO-2005/087272 A2 | 9/2005 | |
| WO | WO-2007/089632 A2 | 8/2007 | |
| WO | WO-2009/013290 A1 | 1/2009 | |
| WO | WO-2009/043936 A1 | 4/2009 | |
| WO | WO-2009/137006 A2 | 11/2009 | |
| WO | WO-2010/071832 A1 | 6/2010 | |
| WO | WO 2010088560 * | 8/2010 | |
| WO | WO-2010/0129021 A1 | 11/2010 | |
| WO | WO-2011/112902 A2 | 9/2011 | |
| WO | WO-2011/133890 A1 | 10/2011 | |

OTHER PUBLICATIONS

Duque et al, Intravenous Administration of Self-complementary AAV9 Enables Transgene Delivery to Adult Motor Neuron, Molecular Therapy, 2009, pp. 1187-1196.*
Wang et al, translation of CN 101137755, EFD Apr. 14, 2004.*
Jalanko et al, Neuronal ceroid lipofuscinoses , Biochimica et Biophysica Acta, 2009, pp. 697-709.*
Abbott et al., Astrocyte-endothelial interactions at the blood-brain barrier, Nat. Rev. Neurosci., 7(1):41-53 (2006).
Abbott et al., Transporting therapeutics across the blood-brain barrier, Mol. Med. Today, 2(3):106-13 (1996).
Abbott, Astrocyte-endothelial interactions and blood-brain barrier permeability, J. Anat., 200(6):629-38 (2002).
Abbott, pp. 189-208, IN: Dermietzel et al. (eds.), Blood-Brain Interfaces—From Ontology to Artificial Barriers, Wiley-VCH Weinheim Germany (2006).
Akbar et al., The role of MR myelography with intrathecal gadolinium in localization of spinal CSF leaks in patients with spontaneous intracranial hypotension, AJNR Am. J. Neuroradiol. 33:535-40(2012).
Al-Sarraf et al., Changes in the kinetics of the acidic amino acid brain and CSF uptake during development in the rat, Brain Res. Dev. Brain Res., 102(1):127-34 (1997).
Amicus Therapeutics, Amicus establishes gene therapy pipeline for Lysosomal storage disorders (LSDs). Sep. 20, 2018, p. 1-27 (2018).
Avila et al., Trichostatin A increases SMN expression and survival in a mouse model of spinal muscular atrophy, J. Clin. Invest., 117(3):659-71 (2007).
Ayuso et al., High AAV vector purity results in serotype- and tissue-independent enhancement of transduction efficiency, Gene Ther., 17(4):503-10 (2010).
Azzouz et al., Lentivector-mediated SMN replacement in a mouse model of spinal muscular atrophy, J. Clin. Invest., 114(12):1726-31 (2004).
Azzouz et al., VEGF delivery with retrogradely transported lentivector prolongs survival in a mouse ALS model, Nature, 429(6990):413-7 (2004).
Ballas et al., Non-cell autonomous influence of MeCP2-deficient glia on neuronal dendritic morphology, Nat. Neurosci., 12(3):311-7 (2009).
Bauer et al., Neural induction of the blood-brain barrier: still an enigma, Cell Mol. Neurobiol., 20(1):13-28 (2000).
Baughan et al., Stimulating full-length SMN2 expression by delivering bifunctional RNAs via a viral vector, Mol. Ther., 14(1):54-62 (2006).
Begley et al., Structural and functional aspects of the blood-brain barrier, Prog. Drug Res., 61:40-78 (2003).
Behnsen, Zeit Zellforsch Mikrosk Anat., 4:515-72 (1905).
Bevan et al., Systemic gene delivery in large species for targeting spinal cord, brain, and peripheral tissues for pediatric disorders, Mol. Ther., 19(11):1971-80 (2011).
Bowerman et al., Therapeutic strategies for spinal muscular atrophy: SMN and beyond, *Disease Models & Mechanisms*. 10:943-54 (2017).
Bryan et al., Implications of protein fold switching, Curr. Opin. in Struct. Biol., 23(2): 314-316, (2013).
Butchbach et al., Abnormal motor phenotype in the SMNDelta7 mouse model of spinal muscular atrophy, Neurobiol. Dis., 27(2):207-19 (2007).
Cabrera-Salazar et al., Timing of therapeutic intervention determines functional and survival outcomes in a mouse model of late infantile batten disease, *Mol. Ther*. 15:1782-88 (2007).
Caley et al., Development of the blood vessels and extracellular spaces during postnatal maturation of rat cerebral cortex, J. Comp. Neurol., 138(1):31-47 (1970).
Carter, "Adeno-Associated Virus Vectors in Clinical Trials", Human Gene Therapy, 16:541-550 (2005).
Carter, Adeno-associated virus vectors, Curr. Opin. Biotechnol., 1533-539 (1992).
Cearley et al., Expanded repertoire of AAV vector serotypes mediate unique patterns of transduction in mouse brain, Mol. Ther., 16(10):1710-8 (2008).
Cearley et al., Transduction characteristics of adeno-associated virus vectors expressing cap serotypes 7, 8, 9, and Rh10 in the mouse brain, Mol. Ther., 13(3):528-37 (2006).
Chang et al., Treatment of spinal muscular atrophy by sodium butyrate, Proc. Natl. Acad. Sci. USA, 98(17):9808-13 (2001).
Chen et al., Deficiency of methyl-CpG binding protein-2 in CNS neurons results in a Rett-like phenotype in mice, Nat. Genet., 27(3):327-31 (2001).
Clark et al., A stable cell line carrying adenovirus-inducible rep and cap genes allows for infectivity titration of adeno-associated virus vectors, Gene Ther., 3(12):1124-32 (1996).
Clark et al., Development of enzymes of energy metabolism in the neonatal mammalian brain, Dev. Neurosci., 15(3-5):174-80 (1993).
Clark et al., Highly purified recombinant adeno-associated virus vectors are biologically active and free of detectable helper and wild-type viruses, Hum. Gene Ther., 10(6):1031-9 (1999).
Costa et al., Developmental neuropathology of environmental agents, Annu. Rev. Pharmacol. Toxicol., 44:87-110 (2004).

(56) References Cited

OTHER PUBLICATIONS

Cotman et al., Cin3Dex7/8 knock-in mice with the common JNCL mutation exhibit progressive neurologic disease that begins before birth, *Hum. Mol. Gen.* 11(22) (2002).
Cressant et al., Improved Behavior and Neuropathology in the Mouse Model of Sanfilippo Type IIIB Disease after Adeno-Associated Virus-Mediated Gene Transfer in the Striatum, *The Journal of Neuroscience.* 24:10229-10239 (2004).
Cserr et al., Blood-brain interfaces in vertebrates: a comparative approach, Am. J. Physiol., 246:277-87 (1984).
Davson et al., Symposium on membrane transport. Transport in the central nervous system, Proc. R. Soc. Med., 60(4):326-9 (1967).
Dayton et al., The advent of AAV9 expands applications for brain and spinal cord gene delivery, *Expert Opin. Biol. Ther.* 12:757-66 (2012).
De et al., High levels of persistent expression of alpha1-antitrypsin mediated by the nonhuman primate serotype rh. 10 adeno-associated virus despite preexisting immunity to common human adeno-associated viruses, Mol. Ther., 13(1):67-76 (2006).
De los Reyes et al., Abstract #204. Interim Results from the First Clinical Gene Therapy Trial for CLN6 Batten Disease. Forty-Eighth National Meeting of the Child Neurology Society. Charlotte, NC. Oct. 23-26, 2019.
Dehouck et al., An easier, reproducible, and mass-production method to study the blood-brain barrier in vitro, J. Neurochem., 54(5):1798-801 (1990).
Del Gaudio et al., Increased MECP2 gene copy number as the result of genomic duplication in neurodevelopmentally delayed males, Genet. Med., 8(12):784-92 (2006).
Dodge et al., Delivery of AAV-IGF-1 to the CNS extends survival in ALS mice through modification of aberrant glial cell activity, Mol. Ther., 16(6):1056-64 (2008).
Dominguez et al., Intravenous scAAV9 delivery of a codon-optimized SMN1 sequence rescues SMA mice, Hum. Molec. Gen. 20(4):681-693 (2011).
Drory et al., EEG Recordings Following Intrathecal Iohexol Administration, *Clinical Neuropharmacology.* 13(4):318-321 (1990).
Eck et al., Gene-based therapy, Chapter 5 pp. 77-101, IN: Goodman & Gilman's The Pharmacological Basis of Therapeutics, New York, NY: McGraw Hill (1996).
Federici et al., Robust spinal motor neuron transduction following intrathecal delivery of AAV9 in pigs, Gene Ther., 19(8):852-9 (2012).
Ford, Selected maturational changes observed in the postnatal rat brain, Prog. Brain Res., 40(0):1-12 (1973).
Foust et al., Intravascular AAV9 preferentially targets neonatal neurons and adult astrocytes, Nat. Biotechnol., 27(1):59-65 (2009).
Foust et al., Rescue of the spinal muscular atrophy phenotype in a mouse model by early postnatal delivery of SMN, Nat. Biotechnol., 28(3):271-4 (2010).
Fraldi et al., Functional correction of CNS lesions in an MPS-IIIA mouse model by intracerebral AAV-mediated delivery of sulfamidase and SUMF1 genes, Human Molecular Genetics. 16:2693-2702(2007) .
Friez et al., Recurrent infections, hypotonia, and mental retardation caused by duplication of MECP2 and adjacent region in Xq28, *Pediatrics.* 118(6):e1687-95 (2006).
Fu et al., Self-complementary adeno-associated virus serotype 2 vector: global distribution and broad dispersion of AAV-mediated transgene expression in mouse brain, Mol. Ther., 8(6):911-7 (2003).
Gadalla et al., Improved survival and reduced phenotypic severity following AAV9/MECP2 gene transfer to neonatal and juvenile male Mecp2 knockout mice, *Mol. Ther.* 21(1):18-30 (2013).
Gao et al., Clades of Adeno-associated viruses are widely disseminated in human tissues, J. Virol., 78(12):6381-8 (2004).
Gao et al., Mutations in a novel CLN6-encoded transmembrane protein cause variant neuronal ceroid lipofuscinosis in man and mouse, *Am. J. Hum. Genet.* 70:324-35 (2002).

Gavrilina et al., Neuronal SMN expression corrects spinal muscular atrophy in severe SMA mice while muscle-specific SMN expression has no phenotypic effect, Hum. Mol. Genet., 17(8):1063-75 (2008).
Genetics Home Reference, 2020, Lister Hill Natinal Center for Biomedical Communications, US National Library of Medicine, NIH, DHHS, p. 1-6.
Grady et al., Cerebellar synaptic defects and abnormal motor behavior in mice lacking alpha- and beta-dystrobrevin, J. Neurosci., 26(11):2841-51 (2006).
Gray et al., Viral vectors and delivery strategies for CNS gene therapy, *Ther. Deliv.* 1:1-29 (2010).
Griffey et al., CNS-Directed AAV2-Mediated Gene Therapy Ameliorates Functional Deficits in a Murine Model of Infantile Neuronal Ceroid Lipofuscinosis, *Molecular Therapy.* 13:538-547(2005).
Guy et al., A mouse Mecp2-null mutation causes neurological symptoms that mimic Rett syndrome, *Nat. Genet.*, 27(3):322-6 (2001).
Guy et al., Reversal of neurological defects in a mouse model of Rett syndrome, Science, 315(5815):1143-7 (2007).
Haria et al., Iohexol a review of its pharmacological properties and use as a contrast medium in Myelography and Neuroangiography. *CNS Drugs.* 7:229-255 (1997).
Haseloff et al., In search of the astrocytic factor(s) modulating blood-brain barrier functions in brain capillary endothelial cells in vitro, Cell Mol. Neurobiol., 25(1):25-39 (2005).
Hawkins et al., The blood-brain barrier/neurovascular unit in health and disease, Pharmacol. Rev., 57(2):173-85 (2005).
Hayashi et al., Induction of various blood-brain barrier properties in non-neural endothelial cells by close apposition to co-cultured astrocytes, Glia, 19(1):13-26 (1997).
Hermonat et al., Use of adeno-associated virus as a mammalian DNA cloning vector: transduction of neomycin resistance into mammalian tissue culture cells, Proc. Natl. Acad. Sci. USA, 81(20):6466-70 (1984).
Highlights of Prescribing Information Omnipaque- iohexol injection, GE Healthcare Inc. (May 2018).
Hsieh-Li et al., A mouse model for spinal muscular atrophy, Nat. Genet., 24(1):66-70 (2008).
Hudry et al., Therapeutic AAV gene transfer to the newvous system: A clinical reality, Neuron 101, 839-62 (Mar. 6, 2019).
Iadecola, Neurovascular regulation in the normal brain and in Alzheimer's disease, Nat. Rev. Neurosci., 5(5):347-60 (2004).
Inagaki et al., Robust systemic transduction with AAV9 vectors in mice: efficient global cardiac gene transfer superior to that of AAV8, Mol. Ther., 14(1):45-53 (2006).
Inagaki, et al., "Robust Systemic Transduction with AAV9 Vectors in Mice: Efficient Global Cardiac Gene Transfer Superior to That of AAV8," Molecular Therapy, vol. 14, No. 1, pp. 45-53 (Jul. 2006).
Kaiser, Clinical research. Death prompts a review of gene therapy vector, Science, 317(5838):580 (2007).
Kaminsky and Ascano, Rett Syndrome Gene Therapy: Understanding the Published Data, (2017).
Kaplitt et al., Safety and tolerability of gene therapy with an adeno-associated virus (AAV) borne GAD gene for Parkinson's disease: an open label, phase I trial, Lancet, 369(9579):2097-105 (2007).
Kaspar et al., Retrograde viral delivery of IGF-1 prolongs survival in a mouse ALS model, Science, 301(5634):839-42 (2003).
Katz et al., Preclinical research in Rett syndrome: setting the foundation for translational success, Dis. Model Mech., 5(6):733-45 (2012).
Kempermann et al., Genetic influence on neurogenesis in the dentate gyrus of adult mice, Proc. Natl. Acad. Sci. USA, 94(19):10409-14 (1997).
Klein et al., AAV8, 9, Rh10, Rh43 vector gene transfer in the rat brain: effects of serotype, promoter and purification method, Mol. Ther., 16(1):89-96 (2008).
Kohan et al., Therapeutic approaches to the challenge of neuronal ceroid lipofuscinoses, Curr. Pharm. Biotechnol., 12(6):867-83 (2011).
Kong et al., Impaired synaptic vesicle release and immaturity of neuromuscular junctions in spinal muscular atrophy mice, J. Neurosci., 29(3):842-51 (2009).

(56) References Cited

OTHER PUBLICATIONS

Kota et al., Follistatin gene delivery enhances muscle growth and strength in nonhuman primates, Sci. Transl. Med., 1:6-15 (2009).
Kotterman et al., Engineering adeno-associated viruses for clinical gene therapy, Nat. Rev. 15:445-51 (2014).
Laughlin et al., Cloning of infectious adeno-associated virus genomes in bacterial plasmids, Gene, 23(1):65-73 (1983).
Le et al., SMNDelta7, the major product of the centromeric survival motor neuron (SMN2) gene, extends survival in mice with spinal muscular atrophy and associates with full-length SMN, Hum. Mol. Genet., 14(6):845-57 (2005).
Lebkowski et al., Adeno-associated virus: a vector system for efficient introduction and integration of DNA into a variety of mammalian cell types, Mol. Cell. Biol. 8:3988-96 (1988).
Lenzi et al., 2014, NCBI Bookshelf, A service of the national library of medicine, National Institute of Health, Oversight and review of clinical gene transfer protocols: Assessing the role of the recombinant DNA advisory committee. Washington (DC): National Academies Press (US), pp. 1-16.
Lioy et al., A role for glia in the progression of Rett's syndrome, Nature, 475:497-500 (2011).
Maguire et al., Gene therapy for the nervous system: challenges and new strategies, Neurotherapeutics. 11:817-39 (2014).
Maqbool et al., The substrate-binding protein in bacterial ABC transporters: dissecting roles in the evolution of substrate specificity, Biochem. Soc. Trans. 43:1011-7 (2015).
Marks et al., Safety and tolerability of intraputaminal delivery of CERE-120 (adeno-associated virus serotype 2-neurturin) to patients with idiopathic Parkinson's disease: an open-label, phase I trial, Lancet Neurol., 7(5):400-8 (2008).
McAllister et al., Mechanisms of glucose transport at the blood-brain barrier: an in vitro study, Brain Res., 904(1):20-30 (2001).
McCarty et al., Adeno-associated virus terminal repeat (TR) mutant generates self-complementary vectors to overcome the rate-limiting step to transduction in vivo, Gene Ther., 10(26):2112-8 (2003).
McCarty et al., Self-complementary AAV Vectors; Advances and Applicaitons, Amer. Soc. Gene. Ther., 16(10):1648-56 (2008).
McCarty et al., Self-complementary recombinant adeno-associated virus (scAAV) vectors promote efficient transduction independently of DNA synthesis, Gene Therapy. 8:1248-1254 (2001).
McIlwain, "Chemical and enzymic make-up of the brain during development" IN: McIlwain, Biochemistry and the Central Nervous System, London: Churchill Livingstone (1966).
McLaughlin et al., Adeno-associated virus general transduction vectors: analysis of proviral structures, J. Virol., 62(6):1963-73 (1988).
Mingozzi et al., Therapeutic in vivo gene transfer for genetic disease using AAV: progress and challenges, Nat. Rev. Genet. 12:341-55 (2011).
Monani et al., A transgene carrying an A2G missense mutation in the SMN gene modulates phenotypic severity in mice with severe (type I) spinal muscular atrophy, J. Cell Biol., 160(1):41-52 (2003).
Monani et al., The human centromeric survival motor neuron gene (SMN2) rescues embryonic lethality in Smn(-/-) mice and results in a mouse with spinal muscular atrophy, Hum. Mol. Genet., 9(3):333-9 (2000).
Mori et al., Two novel adeno-associated viruses from cynomolgus monkey: pseudotyping characterization of capsid protein, Virology, 330(2):375-83 (2004).
Muzyczka, Use of adeno-associated virus as a general transduction vector for mammalian cells, Curr. Top. Microbiol. Immunol. 158:97-129 (1992).
Narver et al., Sustained improvement of spinal muscular atrophy mice treated with trichostatin A plus nutrition, Ann. Neurol., 64(4):465-70 (2008).
NCBI Accession No. U30894.1, Human N-sulphoglucosamine sulphohydrolase mRNA, complete cds, dated Feb. 2, 1996.
Oertle et al., Nogo-A inhibits neurite outgrowth and cell spreading with three discrete regions, J. Neurosci., 23(13):5393-406 (2003).
Olsen et al., Intrathecal iohexol-distribution following cervical myelography, postmyelographic registration of adverse effects, psychometric assessment and electroencephalographic recording, Acta Neurol. Scand. 82:321-8 (1990).
Oprea et al., Plastin 3 is a protective modifier of autosomal recessive spinal muscular atrophy, Science, 320(5875):524-7 (2008).
Pacak et al., Recombinant adeno-associated virus serotype 9 leads to preferential cardiac transduction in vivo, Circ. Res., 99(4):e3-9 (2006).
Palli et al., Improved ecdysone receptor-based inducible gene regulation system, Eur. J. Biochem., 270(6):1308-15 (2003).
Papisov et al., Physiology of the intrathecal bolus: the leptomeningeal route for macromolecule and particle delivery to CNS, Mol. Pharm. 10:1522-1532 (2013).
Pardridge, Drug and gene targeting to the brain with molecular Trojan horses, Nat. Rev. Drug Discov., 1(2):131-9 (2002).
Paul et al., Increased viral titer through concentration of viral harvests from retroviral packaging lines, Hum. Gene Ther., 4(5):609-15 (1993).
Penta, Sulla colorazione vitale del sistema nervoso central negli animali neonati, Riv. di Neurol., 5:62-80 (1932).
Perabo et al., Combinatorial engineering of a gene therapy vector: directed evolution of adeno-associated virus, The Journal of Gene Medicine. 8:155-162 (2005).
Perrin et al., An experimental rabies vaccine produced with a new BHK-21 suspension cell culture process: use of serum-free medium and perfusion-reactor system, Vaccine, 13(13):1244-50 (1995).
Ralph et al., Silencing mutant SOD1 using RNAi protects against neurodegeneration and extends survival in an ALS model, Nat. Med., 11(4):429-33 (2005).
Rastegar et al., MECP2 isoform-specific vectors with regulated expression for Rett syndrome gene therapy, PLoS One, 4(8):e6810 (2009).
Ratcliff et al., Cognitive and affective changes after myelography: A Comparison of Metrizamide and Iohexol, Am. J. Roentgenol., 147:777-81 (1986).
Reichenbach et al., pp. 19-35 IN: Kettemann et al., Neuroglia, 2nd ed., New York: Oxford University Press (2004).
Risau et al., Development of the blood-brain barrier, Trends Neurosci., 13(5):174-8 (1990).
Risau et al., Differentiation-dependent expression of proteins in brain endothelium during development of the blood-brain barrier, Dev. Biol., 117(2):537-45 (1986).
Robinson et al., Morphological and functional reversal of phenotypes in a mouse model of Rett syndrome, Brain, 135(Pt. 9):2699-710 (2012).
Royo et al., Specific AAV serotypes stably transduce primary hippocampal and cortical cultures with high efficiency and low toxicity, Brain Res., 1190:15-22 (2008).
Rubin et al., A cell culture model of the blood-brain barrier, J. Cell Biol., 115(6):1725-35 (1991).
Ruffing et al., Mutations in the carboxy terminus of adeno-associated virus 2 capsid proteins affect viral infectivity: lack of an RGD integrin-binding motif, J. Gen. Virol., 75(Pt. 12):3385-92 (1994).
Samulski et al., Cloning of adeno-associated virus into pBR322: rescue of intact virus from the recombinant plasmid in human cells, Proc. Natl. Acad. Sci. USA, 79(6):2077-81 (1982).
Samulski et al., Helper-free stocks of recombinant adeno-associated viruses: normal integration does not require viral gene expression, J. Virol., 63(9):3822-8 (1989).
Saunders et al., On the progestational activity of 17alpha-ethynyl-17-hydroxy-5(10)-estren-3-one (norethynodrel), Endocrinology, 60(6):804-5 (1957).
Schlageter et al., Microvessel organization and structure in experimental brain tumors: microvessel populations with distinctive structural and functional properties, Microvasc. Res., 58(3):312-28 (1999).
Schnepp et al., Highly purified recombinant adeno-associated virus vectors. Preparation and quantitation, Methods Mol. Med. 69:427-43 (2002).
Schuster et al., Biodistribution of adeno-associated virus serotype 9 (AAV9) vector after intrathecal and intravenous delivery in mouse, Front Neuroanat. 8:42 (2014).

(56) References Cited

OTHER PUBLICATIONS

Senapathy et al., Molecular cloning of adeno-associated virus variant genomes and generation of infectious virus by recombination in mammalian cells, J. Biol. Chem., 259(7):4661-6 (1984).
Shim et al., Nonviral delivery systems for cancer gene therapy: Strategies and challenges, *Curr. Gene Ther.* 17:1-18 (2017).
Siegel et al., Francis Crick's legacy for neuroscience: between the alpha and the Omega, PLoS Biol., 2(12):e419 (2004).
Sinnett et al., Recent endeavors in MECP2 gene transfer for gene therapy of Rett syndrome, *Discov. Med.* 24:153-9 (2017).
Skene et al., Neuronal MeCP2 is expressed at near histone-octamer levels and globally alters the chromatin state, Mol. Cell, 37(4):457-68 (2010).
Snyder et al., Comparison of adeno-associated viral vector serotypes for spinal cord and motor neuron gene delivery, *Hum. Gene. Ther.*, 22(9):1129-35 (2011).
Sobue et al., Induction of blood-brain barrier properties in immortalized bovine brain endothelial cells by astrocytic factors, *Neurosci. Res.*, 35(2):155-64 (1999).
Sondhi et al., Correction of the lysosomal storage defect in mouse model of juvenile neuronal ceroid lipofuscinosis by neonatal injection of AAV serotype rh. 10 vector expressing the human, *Mol. Ther.* 19:S78 (2011).
Srivastava et al., Nucleotide sequence and organization of the adeno-associated virus 2 genome, J. Virol., 45(2):555-64 (1983).
Steinfeld et al., Late Infantile Neuronal Ceroid Lipofuscinosis: Quantitative Description of the Clinical Course in Patients With CLN2 Mutations, *Am. J. Med. Genetics.* 112:347-54 (2002).
Stern et al., Platelet lipoxygenase in spontaneously hypertensive rats, Hypertension, 27(5):1149-52 (1996).
Stewart et al., Interendothelial junctional changes underlie the developmental 'tightening' of the blood-brain barrier, Brain Res., 429(2):271-81 (1987).
Stoodley et al., Effect of Adenovirus-mediated Nitric Oxide Synthase Gene Transfer on Vasospasm after Experimental Subarachnoid hemorrhage, Nuerosurg., 46(5):1193-1203 (2000).
Storek et al., Sensory neuron targeting by self-complementary AAV8 via lumbar puncture for chronic pain, PNAS. 105:1055-1060 (2008).
Su et al., Real-time MR imaging with Gadoteridol predicts distribution of transgenes after convection-enhanced delivery of AAV2 vectors, *Mol. Ther.* 18:1490-5 (2010).
Suzuki et al., Are animal models useful for understanding the pathophysiology of lysosomal storage disease?, *Acta. Paediatr. Suppl.* 92:54-62 (2003).
Towne et al., Recombinant adeno-associated virus serotype 6 (rAAV2/6)-mediated gene transfer to nociceptive neurons through different routes of delivery, Molecular Pain. 5:1-17 (2009).
Traschin et al., A human parvovirus, adeno-associated virus, as a eucaryotic vector: transient expression and encapsidation of the procaryotic gene for chloramphenicol acetyltransferase, Mol. Cell Biol., 4:2072-81 (1984).
Tratschin et al., Adeno-associated virus vector for high-frequency integration, expression, and rescue of genes in mammalian cells, Mol. Cell Biol., 5(11):3251-60 (1985).

Turner et al., Administration of substances to laboratory animals: routes of administration and factors to consider, *J. Am. Assoc. Lab Anim. Sci.*, 50(5):600-13 (2011).
Urlinger et al., Exploring the sequence space for tetracycline-dependent transcriptional activators: novel mutations yield expanded range and sensitivity, Proc. Natl. Acad. Sci. USA, 97(14):7963-8 (2000).
Verkman, Aquaporin water channels and endothelial cell function, J. Anat., 200(6):617-27 (2002).
Vestergaard et al., Central Nervous System Reactions to Cervical Myelography, *Acta Radiol.* Sep.; 32:411-4 (1999).
Virgintino et al., Immunolocalization of tight junction proteins in the adult and developing human brain, Histochem. Cell Biol., 122(1):51-9 (2004).
Vorbrodt et al., Localization of alkaline phosphatase activity in endothelia of developing and mature mouse blood-brain barrier, *Dev. Neurosci.* 8:1-13 (1986).
Wang et al., Adeno-associated virus serotype 8 efficiently delivers genes to muscle and heart, Nat. Biotechnol., 23(3):321-8 (2005).
Wang et al., Decreased synaptic activity shifts the calcium dependence of release at the mammalian neuromuscular junction in vivo, J. Neurosci., 24(47):10687-92 (2004).
Wang et al., Expansive gene transfer in the rat CNS rapidly produces amyotrophic lateral sclerosis relevant sequelae when TDP-43 is overexpressed, *Mol. Ther.* 18:2064-74 (2010).
Watson et al., Postnatal growth and morphological development of the brain: a species comparison, Birth Defects Res. B Dev. Reprod. Toxicol., 77(5):471-84 (2006).
Wolburg et al., Tight junctions of the blood-brain barrier: development, composition and regulation, Vascul. Pharmacol., 38(6):323-37 (2002).
Wolburg, pp. 77-107 IN: Dermietzel et al., (eds.), Blood-Brain Interfaces—from Ontogeny to Artificial Barriers, Wiley-VCH (2006).
Worgall et al., Treatment of late infantile neuronal ceroid lipofuscinosis by CNS administration of a serotype 2 adeno-associated virus expressing CLN2 cDNA, Hum. Gene Ther., 19(5):463-74 (2008).
Wu et al., Optimization of Self-complementary AAV Vectors for Liver-directed Expression Results in Sustained Correction of Hemophilia B at Low Vector Dose, The American Society of Gene Therapy. 16:280-289 (2008).
Wu et al., Single amino acid changes can influence titer, heparin binding, and tissue tropism in different adeno-associated virus serotypes, Journal of Virology. 80:11393-11397 (2006).
Xiao et al., Gene therapy vectors based on adeno-associated virus type 1, *J. Virol.* 73:3994-4003 (1999).
Yamanaka et al., Astrocytes as determinants of disease progression in inherited amyotrophic lateral sclerosis, *Nat. Neurosci*, 11(3):251-3 (2008).
Zincarelli et al., Analysis of AAV Serotypes 1-9 Mediated Gene Expression and Tropism in Mice After Systemic Injection, Molecular Therapy. 16:1073-1080 (2008).
Foust et al. Retraction Note: Rescue of the spinal muscular atrophy phenotype in a mouse model by early postnatal delivery of SMN, Nature Med. 40: 1692 (2022).

\* cited by examiner

SEQUENCE LISTING

```
<160> NUMBER OF SEQ ID NOS: 1

<210> SEQ ID NO 1
<211> LENGTH: 6042
<212> TYPE: DNA
<213> ORGANISM: adeno-associated virus 9
<220> FEATURE:
<221> NAME/KEY: misc_feature
<222> LOCATION: (980)..(3336)
<223> OTHER INFORMATION: Vector genome insert
<220> FEATURE:
<221> NAME/KEY: misc_feature
<222> LOCATION: (980)..(1085)
<223> OTHER INFORMATION: Mutated ITR
<220> FEATURE:
<221> NAME/KEY: misc_feature
<222> LOCATION: (1132)..(1411)
<223> OTHER INFORMATION: CMV enhancer
<220> FEATURE:
<221> NAME/KEY: misc_feature
<222> LOCATION: (1418)..(1687)
<223> OTHER INFORMATION: Chicken beta-Actin promoter
<220> FEATURE:
<221> NAME/KEY: misc_feature
<222> LOCATION: (1753)..(1812)
<223> OTHER INFORMATION: Modified SV40 late 16s intron
<220> FEATURE:
<221> NAME/KEY: misc_feature
<222> LOCATION: (1753)..(1783)
<223> OTHER INFORMATION: SV40 late 19s intron
<220> FEATURE:
```

```
<221> NAME/KEY: misc_feature
<222> LOCATION: (1982)..(2866)
<223> OTHER INFORMATION: hSMN
<220> FEATURE:
<221> NAME/KEY: misc_feature
<222> LOCATION: (2970)..(3116)
<223> OTHER INFORMATION: BGHpA
<220> FEATURE:
<221> NAME/KEY: misc_feature
<222> LOCATION: (3196)..(3336)
<223> OTHER INFORMATION: ITR

<400> SEQUENCE: 1
gcccaatacg caaaccgcct ctccccgcgc gttggccgat tcattaatgc agctggcgta      60
atagcgaaga ggcccgcacc gatcgccctt cccaacagtt gcgcagcctg aatggcgaat     120
ggcgattccg ttgcaatggc tggcggtaat attgttctgg atattaccag caaggccgat     180
agtttgagtt cttctactca ggcaagtgat gttattacta atcaaagaag tattgcgaca     240
acggttaatt tgcgtgatgg acagactctt ttactcggtg gcctcactga ttataaaaac     300
acttctcagg attctggcgt accgttcctg tctaaaatcc ctttaatcgg cctcctgttt     360
agctcccgct ctgattctaa cgaggaaagc acgttatacg tgctcgtcaa agcaaccata     420
gtacgcgccc tgtagcggcg cattaagcgc ggcgggtgtg gtggttacgc gcagcgtgac     480
cgctacactt gccagcgccc tagcgcccgc tcctttcgct ttcttccctt cctttctcgc     540
cacgttcgcc ggctttcccc gtcaagctct aaatcggggg ctcccttag ggttccgatt     600 tagtgcttta cggcacctcg accccaaaaa acttgattag ggtgatggtt cacgtagtgg     660
gccatcgccc tgatagacgg ttttcgccc tttgacgttg gagtccacgt tctttaatag     720
tggactcttg ttccaaactg gaacaacact caaccctatc tcggtctatt cttttgattt     780
ataagggatt ttgccgattt cggcctattg gttaaaaaat gagctgattt aacaaaaatt     840
taacgcgaat tttaacaaaa tattaacgct tacaatttaa atatttgctt atacaatctt     900
cctgtttttg ggcttttct gattatcaac cggggtacat atgattgaca tgctagtttt     960
acgattaccg ttcatcgccc tgcgcgctcg ctcgctcact gaggccgccc gggcaaagcc    1020
cgggcgtcgg gcgacctttg gtcgcccggc ctcagtgagc gagcgagcgc gcagagaggg    1080
agtggaattc acgcgtggat ctgaattcaa ttcacgcgtg gtacctctgg tcgttacata    1140
acttacggta atggcccgc ctggctgacc gcccaacgac ccccgcccat tgacgtcaat    1200
aatgacgtat gttcccatag taacgccaat agggactttc cattgacgtc aatgggtgga    1260
gtatttacgg taaactgccc acttggcagt acatcaagtg tatcatatgc caagtacgcc    1320
ccctattgac gtcaatgacg gtaaatggcc cgcctggcat tatgcccagt acatgacctt    1380
atgggacttt cctacttggc agtacatcta cgtatgagcca cgttctgctt cactctcccc    1440 atctccccc cctccccacc cccaattttg tatttattta ttttttaatt attttgtgca    1500
gcgatggggg cggggggggg gggggggcgc gcgccaggcg gggcggggcg gggcgagggg    1560
cggggcgggg cgaggcggag aggtgcgcg gcagccaatc agagcggcgc gctccgaaag    1620 tttccttttta tggcgaggcg gcggcggcgg cggccctata aaaagcgaag cgcgcggcgg    1680
gcgggagcgg gatcagccac cgcggtggcg gcctagagtc gacgaggaac tgaaaaacca    1740
gaaagttaac tggtaagttt agtctttttg tcttttattt caggtcccgg atccggtggt    1800
ggtgcaaatc aaagaactgc tcctcagtgg atgttgcctt tacttctagg cctgtacgga    1860
agtgttactt ctgctctaaa agctgcggaa ttgtacccgc ggccgatcca ccggtccgga    1920
attcccggga tatcgtcgac ccacgcgtcc gggcccacg ctgcgcaccc gcgggtttgc    1980
```

```
tatggcgatg agcagcggcg gcagtggtgg cggcgtcccg gagcaggagg attccgtgct    2040
gttccggcgc ggcacaggcc agagcgatga ttctgacatt tgggatgata cagcactgat    2100
aaaagcatat gataaagctg tggcttcatt taagcatgct ctaaagaatg gtgacatttg    2160
tgaaacttcg ggtaaaccaa aaaccacacc taaaagaaaa cctgctaaga agaataaaag    2220
ccaaaagaag aatactgcag cttccttaca acagtggaaa gttggggaca aatgttctgc    2280
catttggtca gaagacggtt gcatttaccc agctaccatt gcttcaattg attttaagag    2340
agaaacctgt gttgtggttt acactggata tggaaataga gaggagcaaa atctgtccga    2400
tctactttcc ccaatctgtg aagtagctaa taatatagaa cagaatgctc aagagaatga    2460
aaatgaaagc caagtttcaa cagatgaaag tgagaactcc aggtctcctg gaaataaatc    2520
agataacatc aagcccaaat ctgctccatg gaactctttt ctccctccac caccccccat    2580
gccagggcca agactgggac caggaaagcc aggtctaaaa ttcaatggcc caccaccgcc    2640
accgccacca ccaccacccc acttactatc atgctggctg cctccatttc cttctggacc    2700
accaataatt cccccaccac ctcccatatg tccagattct cttgatgatg ctgatgcttt    2760
gggaagtatg ttaatttcat ggtacatgag tggctatcat actggctatt atatgggttt    2820
tagacaaaat caaaagaag gaaggtgctc acattcctta aattaaggag aaatgctggc    2880
atagagcagc actaaatgac accactaaag aaacgatcag acagatctag aaagcttatc    2940
gataccgtcg actagagctc gctgatcagc ctcgactgtg ccttctagtt gccagccatc    3000
tgttgtttgc cctcccccg tgccttcctt gaccctggaa ggtgccactc ccactgtcct    3060
ttcctaataa aatgaggaaa ttgcatcgca ttgtctgagt aggtgtcatt ctattctggg    3120
gggtggggtg gggcaggaca gcaaggggga ggattggaa gacaatagca ggcatgctgg    3180
ggagagatcg atctgaggaa cccctagtga tggagttggc cactccctct ctgcgcgctc    3240
gctcgctcac tgaggccggg cgaccaaagg tcgcccgacg cccgggcttt gcccgggcgg    3300
cctcagtgag cgagcgagcg cgcagagagg gagtggcccc cccccccccc cccccggcga    3360
ttctcttgtt tgctccagac tctcaggcaa tgacctgata gcctttgtag agacctctca    3420
aaaatagcta ccctctccgg catgaattta tcagctagaa cggttgaata tcatattgat    3480
ggtgatttga ctgtctccgg cctttctcac ccgtttgaat ctttacctac acattactca    3540
ggcattgcat ttaaaatata tgagggttct aaaaattttt atccttgcgt tgaaataaag    3600
gcttctcccg caaagtatt acagggtcat aatgttttg gtacaaccga tttagcttta    3660
tgctctgagg ctttattgct taattttgct aattctttgc cttgcctgta tgatttattg    3720
gatgttggaa tcgcctgatg cggtattttc tccttacgca tctgtgcggt atttcacacc    3780
gcatatggtg cactctcagt acaatctgct ctgatgccgc atagttaagc cagcccgac    3840 acccgccaac actatggtgc actctcagta caatctgctc tgatgccgca tagttaagcc    3900
agccccgaca cccgccaaca cccgctgacg cgccctgacg gcttgtctg ctcccggcat    3960 ccgcttacag acaagctgtg accgtctccg ggagctgcat gtgtcagagg ttttcaccgt    4020
catcaccgaa acgcgcgaga cgaaagggcc tcgtgatacg cctatttta taggttaatg    4080 tcatgataat aatggtttct tagacgtcag gtggcacttt tcggggaaat gtgcgcggaa    4140 ccccctatttg tttatttttc taaatacatt caaatatgta tccgctcatg agacaataac    4200
cctgataaat gcttcaataa tattgaaaaa ggaagagtat gagtattcaa catttccgtg    4260
tcgcccttat tccctttttt gcggcatttt gccttcctgt ttttgctcac ccagaaacgc    4320
```

```
tggtgaaagt aaaagatgct gaagatcagt tgggtgcacg agtgggttac atcgaactgg    4380
atctcaacag cggtaagatc cttgagagtt ttcgccccga agaacgtttt ccaatgatga    4440
gcacttttaa agttctgcta tgtggcgcgg tattatcccg tattgacgcc gggcaagagc    4500
aactcggtcg ccgcatacac tattctcaga atgacttggt tgagtactca ccagtcacag    4560
aaaagcatct tacggatggc atgacagtaa gagaattatg cagtgctgcc ataaccatga    4620
gtgataacac tgcggccaac ttacttctga caacgatcgg aggaccgaag gagctaaccg    4680
cttttttgca caacatgggg gatcatgtaa ctcgccttga tcgttgggaa ccggagctga    4740
atgaagccat accaaacgac gagcgtgaca ccacgatgcc tgtagcaatg gcaacaacgt    4800
tgcgcaaact attaactggc gaactactta ctctagcttc ccggcaacaa ttaatagact    4860
ggatggaggc ggataaagtt gcaggaccac ttctgcgctc ggcccttccg gctggctggt    4920
ttattgctga taaatctgga gccggtgagc gtgggtctcg cggtatcatt gcagcactgg    4980
ggccagatgg taagccctcc cgtatcgtag ttatctacac gacggggagt caggcaacta    5040
tggatgaacg aaatagacag atcgctgaga taggtgcctc actgattaag cattggtaac    5100
tgtcagacca gtttactca tatatacttt agattgattt aaaacttcat tttaattta     5160
aaaggatcta ggtgaagatc cttttgata atctcatgac caaaatccct taacgtgagt    5220
tttcgttcca ctgagcgtca gaccccgtag aaaagatcaa aggatcttct tgagatcctt    5280
tttttctgcg cgtaatctgc tgcttgcaaa caaaaaaacc accgctacca gcggtggttt    5340
gtttgccgga tcaagagcta ccaactcttt ttccgaaggt aactggcttc agcagagcgc    5400
agataccaaa tactgttctt ctagtgtagc cgtagttagg ccaccacttc aagaactctg    5460
tagcaccgcc tacataccte gctctgctaa tcctgttacc agtggctgct gccagtggcg    5520
ataagtcgtg tcttaccggg ttggactcaa gacgatagtt accggataag cgcagcggt    5580
cgggctgaac ggggggttcg tgcacacagc ccagcttgga gcgaacgacc tacaccgaac    5640
tgagatacct acagcgtgag ctatgagaaa gcgccacgct tcccgaaggg agaaaggcgg    5700
acaggtatcc ggtaagcggc agggtcggaa caggagagcg cacgagggag cttccagggg    5760
gaaacgcctg gtatctttat agtcctgtcg ggtttcgcca cctctgactt gagcgtcgat    5820
ttttgtgatg ctcgtcaggg gggcggagcc tatggaaaaa cgccagcaac gcggcctttt    5880
tacggttcct ggccttttgc tggccttttg ctcacatgtt ctttcctgcg ttatcccctg    5940
attctgtgga taaccgtatt accgcctttg agtgagctga taccgctcgc cgcagccgaa    6000
cgaccgagcg cagcgagtca gtgagcgagg aagcggaaga gc                       6042
```

INTRATHECAL DELIVERY OF RECOMBINANT Adeno-ASSOCIATED VIRUS 9

CROSS-REFERENCE TO RELATED APPLICATIONS

This application is a continuation of U.S. patent application Ser. No. 15/997,433, filed on Jun. 4, 2018, which is a continuation of U.S. patent application Ser. No. 14/417,823, filed Jan. 18, 2015, now abandoned, which is a national phase application of PCT Application No. PCT/US13/53065, filed Jul. 31, 2013, which claims priority from U.S. Provisional Application No. 61/678,458 filed Aug. 1, 2012, which are incorporated by reference in their entirety herein.

STATEMENT OF GOVERNMENT INTEREST

This invention was made with Government support under grant no. NS069476 from the National Institutes of Health. The Government has certain rights in the invention.

INCORPORATION BY REFERENCE OF MATERIAL SUBMITTED ELECTRONICALLY

Incorporated by reference in its entirety is a sequence listing in computer-readable form submitted concurrently herewith and identified as follows: ASCII text file named "47099PCT_SeqListing.txt", 8,954 bytes, created 31 Jul. 2013.

FIELD OF THE INVENTION

The present invention relates to Adeno-associated virus type 9 methods and materials useful for intrathecal delivery (i.e., delivery into the space under the arachnoid membrane of the brain or spinal cord) of polynucleotides. Use of the methods and materials is indicated, for example, for treatment of lower motor neuron diseases such as SMA and ALS as well as Pompe disease and lysosomal storage disorders.

BACKGROUND

Large-molecule drugs do not cross the blood-brain-barrier (BBB) and 98% of small-molecules cannot penetrate this barrier, thereby limiting drug development efforts for many CNS disorders [Pardridge, W. M. *Nat Rev Drug Discov* 1: 131-139 (2002)]. Gene delivery has recently been proposed as a method to bypass the BBB [Kaspar, et al., *Science* 301: 839-842 (2003)]; however, widespread delivery to the brain and spinal cord has been challenging. The development of successful gene therapies for motor neuron disease will likely require widespread transduction within the spinal cord and motor cortex. Two of the most common motor neuron diseases are spinal muscular atrophy (SMA) and amyotrophic lateral sclerosis (ALS), both debilitating disorders of children and adults, respectively, with no effective therapies to date. Recent work in rodent models of SMA and ALS involves gene delivery using viruses that are retrogradely transported following intramuscular injection [Kaspar et al., *Science* 301: 839-842 (2003); Azzouz et al., *J Clin Invest* 114: 1726-1731 (2004); Azzouz et al., *Nature* 429: 413-417 (2004); Ralph et al., *Nat Med* 11: 429-433 (2005)]. However, clinical development may be difficult given the numerous injections required to target the widespread region of neurodegeneration throughout the spinal cord, brain stem and motor cortex to effectively treat these diseases. AAV vectors have also been used in a number of recent clinical trials for neurological disorders, demonstrating sustained transgene expression, a relatively safe profile, and promising functional responses, yet have required surgical intraparenchymal injections [Kaplitt et al., *Lancet* 369: 2097-2105 (2007); Marks et al., *Lancet Neurol* 7: 400-408 (2008); Worgall et al., *Hum Gene Ther* (2008)].

SMA is an early pediatric neurodegenerative disorder characterized by flaccid paralysis within the first six months of life. In the most severe cases of the disease, paralysis leads to respiratory failure and death usually by two years of age. SMA is the second most common pediatric autosomal recessive disorder behind cystic fibrosis with an incidence of 1 in 6000 live births. SMA is a genetic disorder characterized by the loss of lower motor neurons (LMNs) residing along the length of the entire spinal cord. SMA is caused by a reduction in the expression of the survival motor neuron (SMN) protein that results in denervation of skeletal muscle and significant muscle atrophy. SMN is a ubiquitously expressed protein that functions in U snRNP biogenesis.

In humans there are two very similar copies of the SMN gene termed SMN1 and SMN2. The amino acid sequence encoded by the two genes is identical. However, there is a single, silent nucleotide change in SMN2 in exon 7 that results in exon 7 being excluded in 80-90% of transcripts from SMN2. The resulting truncated protein, called SMNΔ7, is less stable and rapidly degraded. The remaining 10-20% of transcript from SMN2 encodes the full length SMN protein. Disease results when all copies of SMN1 are lost, leaving only SMN2 to generate full length SMN protein. Accordingly, SMN2 acts as a phenotypic modifier in SMA in that patients with a higher SMN2 copy number generally exhibit later onset and less severe disease.

Therapeutic approaches for SMA have mainly focused on developing drugs for increasing SMN levels or enhancing residual SMN function. Despite years of screening, no drugs have been fully effective for increasing SMN levels as a restorative therapy. A number of mouse models have been developed for SMA. See, Hsieh-Li et al., *Nature Genetics*, 24 (1): 66-70 (2000); Le et al., *Hum. Mol. Genet.*, 14 (6): 845-857 (2005); Monani et al., *J. Cell. Biol.*, 160 (1): 41-52 (2003) and Monani et al., *Hum. Mol. Genet.*, 9 (3): 333-339 (2000). A recent study express a full length SMN cDNA in a mouse model and the authors concluded that expression of SMN in neurons can have a significant impact on symptoms of SMA. See Gavrilina et al., *Hum. Mol. Genet.*, 17(8):1063-1075 (2008).

ALS is another disease that results in loss of muscle and/or muscle function. First characterized by Charcot in 1869, it is a prevalent, adult-onset neurodegenerative disease affecting nearly 5 out of 100,000 individuals. ALS occurs when specific nerve cells in the brain and spinal cord that control voluntary movement gradually degenerate. Within two to five years after clinical onset, the loss of these motor neurons leads to progressive atrophy of skeletal muscles, which results in loss of muscular function resulting in paralysis, speech deficits, and death due to respiratory failure.

The genetic defects that cause or predispose ALS onset are unknown, although missense mutations in the SOD-1 gene occurs in approximately 10% of familial ALS cases, of which up to 20% have mutations in the gene encoding Cu/Zn superoxide dismutase (SOD1), located on chromosome 21. SOD-1 normally functions in the regulation of oxidative stress by conversion of free radical superoxide anions to hydrogen peroxide and molecular oxygen. To date, over 90 mutations have been identified spanning all exons of the SOD-1 gene. Some of these mutations have been used to generate lines of transgenic mice expressing mutant human SOD-1 to model the progressive motor neuron disease and pathogenesis of ALS.

SMA and ALS are two of the most common motor neuron diseases. Recent work in rodent models of SMA and ALS has examined treatment by gene delivery using viruses that are retrogradedly transported following intramuscular injection. See Azzouz et al., *J. Clin. Invest.*, 114: 1726-1731 (2004); Kaspar et al., *Science*, 301: 839-842 (2003); Azzouz et al., *Nature*, 429: 413-417 (2004) and Ralph et al., *Nature Medicine*, 11: 429-433 (2005). Clinical use of such treatments may be difficult given the numerous injections required to target neurodegeneration throughout the spinal cord, brainstem and motor cortex.

Adeno-associated virus (AAV) is a replication-deficient parvovirus, the single-stranded DNA genome of which is about 4.7 kb in length including 145 nucleotide inverted terminal repeat (ITRs). The nucleotide sequence of the AAV serotype 2 (AAV2) genome is presented in Srivastava et al., *J Virol*, 45: 555-564 (1983) as corrected by Ruffing et al., *J Gen Virol*, 75: 3385-3392 (1994). Cis-acting sequences directing viral DNA replication (rep), encapsidation/packaging and host cell chromosome integration are contained within the ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology*, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is infectious as cloned DNA in plasmids which makes construction of recombinant genomes feasible. Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA such as a gene cassette containing a promoter, a DNA of interest and a polyadenylation signal. The rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized Finally, AAV-infected cells are not resistant to superinfection.

Multiple serotypes of AAV exist and offer varied tissue tropism. Known serotypes include, for example, AAV1, AAV2, AAV3, AAV4, AAV5, AAV6, AAV7, AAV8, AAV9, AAV10 and AAV11. AAV9 is described in U.S. Pat. No. 7,198,951 and in Gao et al., *J. Virol.*, 78: 6381-6388 (2004). Advances in the delivery of AAV6 and AAV8 have made possible the transduction by these serotypes of skeletal and cardiac muscle following simple systemic intravenous or intraperitoneal injections. See Pacak et al., *Circ. Res.*, 99(4): 3-9 (1006) and Wang et al., *Nature Biotech.*, 23(3): 321-8 (2005). The use of AAV to target cell types within the central nervous system, though, has required surgical intraparenchymal injection. See, Kaplitt et al., supra; Marks et al., supra and Worgall et al., supra.

There thus remains a need in the art for methods and vectors for delivering polynucleotides to the central nervous system.

SUMMARY

The present invention provides methods and materials useful for intrathecal delivery of polynucleotides to the central nervous system using recombinant a recombinant AAV9 (rAAV9) as a vector.

More specifically, the invention provides methods of delivering a polynucleotide to the central nervous system of a patient in need thereof comprising intrathecal delivery of rAAV9 and a non-ionic, low-osmolar contrast agent to the patient, wherein the rAAV9 comprises a self-complementary genome including the polynucleotide. The polynucleotide is delivered to, for example, the brain, the spinal cord, a glial cell, an astrocyte and/or a lower motor neuron. The non-ionic, low-osmolar contrast agent is, for example, iobitridol, iohexol, iomeprol, iopamidol, iopentol, iopromide, ioversol or ioxilan. In some embodiments, the polynucleotide is a survival motor neuron (SMN) polynucleotide.

The invention also provides methods of treating a neurological disease in a patient in need thereof comprising intrathecal delivery of a rAAV9 and a non-ionic, low-osmolar contrast agent to the patient, wherein the rAAV9 comprises a self-complementary genome including a therapeutic polynucleotide. The neurological disease is, for example, a neurodegenerative disease such as spinal muscular atrophy or amyotrophic lateral sclerosis. The therapeutic polynucleotide is, for example, an SMN polynucleotide. The SMN polynucleotide is delivered, for example, to the brain, the spinal cord, a glial cell, an astrocyte and/or a lower motor neuron. The non-ionic, low-osmolar contrast agent is, for example, iobitridol, iohexol, iomeprol, iopamidol, iopentol, iopromide, ioversol or ioxilan.

DETAILED DESCRIPTION

Therefore, in one aspect, the invention provides a method for intrathecal delivery of a polynucleotide to the central nervous system of a patient comprising administering a rAAV9 with a genome including the polynucleotide. In some embodiments, a non-ionic, low-osmolar contrast agent is also administered to the patient. The non-ionic, low-osmolar contrast agent increases transduction of target cells in the central nervous system of the patient. In some embodiments, the rAAV9 genome is a self-complementary genome. In other embodiments, the rAAV9 genome is a single-stranded genome.

In some embodiments, the polynucleotide is delivered to brain. Areas of the brain contemplated for delivery include, but are not limited to, the motor cortex and the brain stem. In some embodiments, the polynucleotide is delivered to the spinal cord. In some embodiments, the polynucleotide is delivered to a lower motor neuron. Embodiments of the invention employ rAAV9 to deliver polynucleotides to nerve and glial cells. In some embodiments, the glial cell is a microglial cell, an oligodendrocyte or an astrocyte. In some embodiments, the rAAV9 is used to deliver a polynucleotide to a Schwann cell.

Use of methods and materials of the invention is indicated, for example, for treatment of lower motor neuron diseases such as SMA and ALS as well as Pompe disease, lysosomal storage disorders, Glioblastoma multiforme and Parkinson's disease. Lysosomal storage disorders include, but are not limited to, Activator Deficiency/GM2 Gangliosidosis, Alpha-mannosidosis, Aspartylglucosaminuria, Cholesteryl ester storage disease, Chronic Hexosaminidase A Deficiency, Cystinosis, Danon disease, Fabry disease, Farber disease, Fucosidosis, Galactosialidosis, Gaucher Disease (Type I, Type 11, Type III), GMI gangliosidosis (Infantile, Late infantile/Juvenile, Adult/Chronic), I-Cell disease/Mucolipidosis II, Infantile Free Sialic Acid Storage Disease/ISSD, Juvenile Hexosaminidase A Deficiency, Krabbe disease (Infantile Onset, Late Onset), Metachromatic Leukodystrophy, Mucopolysaccharidoses disorders (Pseudo-Hurler polydystrophy/Mucolipidosis IIIA, MPSI Hurler Syndrome, MPSI Scheie Syndrome, MPS I Hurler-Scheie Syndrome, MPS II Hunter syndrome, Sanfilippo syndrome Type A/MPS III A, Sanfilippo syndrome Type B/MPS III B, Sanfilippo syndrome Type C/MPS III C, Sanfilippo syndrome Type D/MPS III D, Morquio Type A/MPS IVA, Morquio Type B/MPS IVB, MPS IX Hyaluronidase Deficiency, MPS VI Maroteaux-Lamy, MPS VII Sly Syndrome, Mucolipidosis I/Sialidosis, Mucolipidosis IIIC, Mucolipidosis type IV), Multiple sulfatase deficiency, Niemann-Pick Disease (Type A, Type B, Type C), Neuronal Ceroid Lipofuscinoses (CLN6 disease (Atypical Late Infantile, Late Onset variant, Early Juvenile), Batten-Spielmeyer-Vogt/Juvenile NCL/CLN3 disease, Finnish Variant Late Infantile CLN5, Jansky-Bielschowsky disease/Late infantile CLN2/TPP1 Disease, Kufs/Adult-onset NCL/CLN4 disease, Northern Epilepsy/variant late infantile CLN8, Santavuori-Haltia/Infantile CLN1/PPT disease, Beta-mannosidosis, Pompe disease/Glycogen storage disease type II, Pycnodysostosis, Sandhoff Disease/Adult Onset/GM2 Gangliosidosis, Sandhoff Disease/GM2 gangliosidosis—Infantile, Sandhoff Disease/GM2 gangliosidosis—Juvenile, Schindler disease, Salla disease/Sialic Acid Storage Disease, Tay-Sachs/GM2 gangliosidosis, Wolman disease.

In further embodiments, use of the methods and materials is indicated for treatment of nervous system disease such as Rett Syndrome, Alzheimer's Disease, Parkinson's Disease, Huntington's Disease, or for treatment of nervous system injury including spinal cord and brain trauma/injury, stroke, and brain cancers.

In another aspect, the invention provides rAAV genomes. The rAAV genomes comprise one or more AAV ITRs flanking a polynucleotide encoding a polypeptide (including, but not limited to, an SMN polypeptide) or encoding siRNA, shRNA, antisense, and/or miRNA directed at mutated proteins or control sequences of their genes. The polynucleotide is operatively linked to transcriptional control DNAs, specifically promoter DNA and polyadenylation signal sequence DNA that are functional in target cells to form a gene cassette. The gene cassette may also include intron sequences to facilitate processing of an RNA transcript when expressed in mammalian cells.

In some embodiments, the rAAV9 genome encodes a trophic or protective factor for treatment of neurodegenerative disorders, including but not limited to Alzheimer's Disease, Parkinson's Disease, Huntington's Disease along with nervous system injury including spinal cord and brain trauma/injury, stroke, and brain cancers. Non-limiting examples of known nervous system growth factors include nerve growth factor (NGF), brain-derived neurotrophic factor (BDNF), neurotrophin-3 (NT-3), neurotrophin-4/5 (NT-4/5), neurotrophin-6 (NT-6), ciliary neurotrophic factor (CNTF), glial cell line-derived neurotrophic factor (GDNF), the fibroblast growth factor family (e.g., FGF's 1-15), leukemia inhibitory factor (LIF), certain members of the insulin-like growth factor family (e.g., IGF-1), the neurturins, persephin, the bone morphogenic proteins (BMPs), the immunophilins, the transforming growth factor (TGF) family of growth factors, the neuregulins, epidermal growth factor (EGF), platelet-derived growth factor (PDGF), vascular endothelial growth factor family (e.g. VEGF 165), follistatin, Hifl, and others. Also generally contemplated are zinc finger transcription factors that regulate each of the trophic or protective factors contemplated herein. In further embodiments, methods to modulate neuro-immune function are contemplated, including but not limited to, inhibition of microglial and astroglial activation through, for example, NFkB inhibition, or NFkB for neuroprotection (dual action of NFkB and associated pathways in different cell types) by siRNA, shRNA, antisense, or miRNA. In still further embodiments, the rAAV9 genome encodes an apoptotic inhibitor (e.g., bcl2, bclxL). Use of a rAAV9 encoding a trophic factor or spinal cord cord injury modulating protein or a suppressor of an inhibitor of axonal growth (e.g., a suppressor of Nogo [Oertle et al., *The Journal of Neuroscience,* 23(13):5393-5406 (2003)] is also contemplated for treating spinal cord injury.

For treatment of neurodegenerative disorders such as Parkinson's disease, the rAAV9 genome encodes in various embodiments Aromatic acid dopa decarboxylase (AADC), Tyrosine hydroxylase, GTP-cyclohydrolase 1 (gtpch1), apoptotic inhibitors (e.g., bcl2, bclxL), glial cell line-derived neurotrophic factor (GDNF), the inhibitory neurotransmitter-amino butyric acid (GABA), or enzymes involved in dopamine biosynthesis. In further embodiments, the rAAV9 genome may encode, for example, modifiers of Parkin and/or synuclein.

For treatment of neurodegenerative disorders such as Alzheimer's disease, in some embodiments, methods to increase acetylcholine production are contemplated. In some embodiments, methods of increasing the level of a choline acetyltransferase (ChAT) or inhibiting the activity of an acetylcholine esterase (AchE) are contemplated.

The rAAV9 genome encodes in some embodiments, siRNA, shRNA, antisense, and/or miRNA for use in methods to decrease mutant Huntington protein (htt) expression for treating a neurodegenerative disorder such as Huntington's disease.

The rAAV9 genome encodes in various embodiments siRNA, shRNA, antisense, and/or miRNA for use in for treatment of neurodegenerative disorders such as ALS. Treatment results in a decrease in the expression of molecular markers of disease, such as TNFα, nitric oxide, peroxynitrite, and/or nitric oxide synthase (NOS).

In some embodiments, the vectors encode short hairpin RNAs directed at mutated proteins such as superoxide dismutase for ALS, or neurotrophic factors such as GDNF or IGF1 for ALS or Parkinson's disease.

In some embodiments, use of materials and methods of the invention is indicated for treating neurodevelopmental disorders such as Rett Syndrome. For embodiments relating to Rett Syndrome, the rAAV9 genome may encode, for example, methyl cytosine binding protein 2 (MeCP2).

"Treatment" comprises the step of administering via the intrathecal route an effective dose, or effective multiple doses, of a composition comprising a rAAV of the invention to an animal (including a human being) in need thereof. If the dose is administered prior to development of a disorder/disease, the administration is prophylactic. If the dose is administered after the development of a disorder/disease, the administration is therapeutic. In embodiments of the invention, an effective dose is a dose that alleviates (either eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival. Examples of disease states contemplated for treatment by methods of the invention are set out above.

Combination therapies are also contemplated by the invention. Combination as used herein includes both simultaneous treatment or sequential treatments. Combinations of methods of the invention with standard medical treatments (e.g., riluzole in ALS) are specifically contemplated, as are combinations with novel therapies.

While delivery to an individual in need thereof after birth is contemplated, intrauteral delivery to a fetus is also contemplated.

Transduction with rAAV may also be carried out in vitro. In one embodiment, desired target cells are removed from the subject, transduced with rAAV and reintroduced into the subject. Alternatively, syngeneic or xenogeneic cells can be used where those cells will not generate an inappropriate immune response in the subject.

Suitable methods for the transduction and reintroduction of transduced cells into a subject are known in the art. In one embodiment, cells can be transduced in vitro by combining rAAV with the cells, e.g., in appropriate media, and screening for those cells harboring the DNA of interest using conventional techniques such as Southern blots and/or PCR, or by using selectable markers. Transduced cells can then be formulated into pharmaceutical compositions, and the composition introduced into the subject by various techniques, such as by injection into the spinal cord.

The rAAV genomes of the invention lack AAV rep and cap DNA. AAV DNA in the rAAV genomes (e.g., ITRs) may be from any AAV serotype for which a recombinant virus can be derived including, but not limited to, AAV serotypes AAV-1. AAV-2, AAV-3, AAV-4, AAV-5, AAV-6, AAV-7, AAV-8, AAV-9, AAV-10 and AAV-11. The nucleotide sequences of the genomes of the AAV serotypes are known in the art. For example, the complete genome of AAV-1 is provided in GenBank Accession No. NC_002077; the complete genome of AAV-2 is provided in GenBank Accession No. NC_001401 and Srivastava et al., J. Virol., 45: 555-564 {1983): the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV-9 genome is provided in Gao et al., J. Virol., 78: 6381-6388 (2004); the AAV-10 genome is provided in Mol. Ther., 13(1): 67-76 (2006); and the AAV-11 genome is provided in Virology, 330(2): 375-383 (2004).

In another aspect, the invention provides DNA plasmids comprising rAAV genomes of the invention. The DNA plasmids are transferred to cells permissible for infection with a helper virus of AAV (e.g., adenovirus, E1-deleted adenovirus or herpesvirus) for assembly of the rAAV genome into infectious viral particles with AAV9 capsid proteins. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. Production of pseudotyped rAAV is disclosed in, for example, WO 01/83692 which is incorporated by reference herein in its entirety. In various embodiments, AAV capsid proteins may be modified to enhance delivery of the recombinant vector. Modifications to capsid proteins are generally known in the art. See, for example, US 2005/0053922 and US 2009/0202490, the disclosures of which are incorporated by reference herein in their entirety.

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hennonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595. The foregoing documents are hereby incorporated by reference in their entirety herein, with particular emphasis on those sections of the documents relating to rAAV production.

The invention thus provides packaging cells that produce infectious rAAV. In one embodiment packaging cells may be stably transformed cancer cells such as HeLa cells, 293 cells and PerC.6 cells (a cognate 293 line). In another embodiment, packaging cells are cells that are not transformed cancer cells such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

In other embodiments, the invention provides rAAV9 (i.e., infectious encapsidated rAAV9 particles) comprising a rAAV genome of the invention. In one aspect of the invention, the rAAV genome is a self-complementary genome.

In another aspect, rAAV are provided such as a rAAV9 named "rAAV SMN." The rAAV SMN genome (nucleotides 980-3336 of SEQ ID NO: 1) has in sequence an AAV2 ITR, the chicken β-actin promoter with a cytomegalovirus enhancer, an SV40 intron, the SMN coding DNA set out in (GenBank Accession Number NM_000344.2), a polyadenylation signal sequence from bovine growth hormone and another AAV2 ITR. Conservative nucleotide substitutions of SMN DNA are also contemplated (e.g., a guanine to adenine change at position 625 of GenBank Accession Number NM_000344.2). The genome lacks AAV rep and cap DNA, that is, there is no AAV rep or cap DNA between the ITRs of the genome. SMN polypeptides contemplated include, but are not limited to, the human SMN1 polypeptide set out in NCBI protein database number NP_000335.1. Also contemplated is the SMN1-modifier polypeptide plastin-3 (PLS3) [Oprea et al., *Science* 320(5875): 524-527 (2008)]. Sequences encoding other polypeptides may be substituted for the SMN DNA.

The rAAV may be purified by methods standard in the art such as by column chromatography or cesium chloride gradients. Methods for purifying rAAV vectors from helper virus are known in the art and include methods disclosed in, for example, Clark et al., *Hum. Gene Ther.*, 10(6): 1031-1039 (1999); Schenpp and Clark, *Methods Mol. Med.*, 69: 427-443 (2002); U.S. Pat. No. 6,566,118 and WO 98/09657.

In another aspect, the invention contemplates compositions comprising rAAV of the present invention. In one embodiment, compositions of the invention comprise a rAAV encoding a SMN polypeptide. In other embodiments, compositions of the present invention may include two or more rAAV encoding different polypeptides of interest.

Compositions of the invention comprise rAAV in a pharmaceutically acceptable carrier. The compositions may also comprise other ingredients such as diluents and adjuvants. Acceptable carriers, diluents and adjuvants are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

Titers of rAAV to be administered in methods of the invention will vary depending, for example, on the particular rAAV, the mode of administration, the treatment goal, the individual, and the cell type(s) being targeted, and may be determined by methods standard in the art. Titers of rAAV may range from about $1\times10^6$, about $1\times10^7$, about $1\times10^8$, about $1\times10^9$, about $1\times10^{10}$, about $1\times10^{11}$, about $1\times10^{12}$, about $1\times10^{13}$ to about $1\times10^{14}$ or more DNase resistant particles (DRP) per ml. Dosages may also be expressed in units of viral genomes (vg). Dosages may also vary based on the timing of the administration to a human. These dosages of rAAV may range from about $1\times10^{11}$ vg/kg, about $1\times10^{12}$, about $1\times10^{13}$, about $1\times10^{14}$, about $1\times10^{15}$, about $1\times10^{16}$ or more viral genomes per kilogram body weight in an adult. For a neonate, the dosages of rAAV may range from about $1\times10^{11}$, about $1\times10^{12}$, about $3\times10^{12}$, about $1\times10^{13}$, about $3\times10^{13}$, about $1\times10^{14}$, about $3\times10^{14}$, about $1\times10^{15}$, about $3\times10^{15}$, about $1\times10^{16}$, about $3\times10^{16}$ or more viral genomes per kilogram body weight.

In another aspect, methods of transducing target cells (including, but not limited to, nerve or glial cells) with rAAV are contemplated by the invention.

The term "transduction" is used to refer to the administration/delivery of a polynucleotide to a target cell either in vivo or in vitro, via a replication-deficient rAAV of the invention resulting in expression of a functional polypeptide by the recipient cell.

Transduction of cells with rAAV of the invention results in sustained expression of polypeptide or RNA encoded by the rAAV. The present invention thus provides methods of administering/delivering rAAV (e.g., encoding SMN protein) of the invention to an animal or a human patient. These methods include transducing nerve and/or glial cells with one or more rAAV of the present invention. Transduction may be carried out with gene cassettes comprising tissue specific control elements. For example, promoters that allow expression specifically within neurons or specifically within astrocytes. Examples include neuron specific enolase and glial fibrillary acidic protein promoters. Inducible promoters under the control of an ingested drug may also be developed.

In some aspects, it is contemplated that the transduction of cells is increased when a vector of the disclosure is used in combination with a contrast agent as described herein relative to the transduction of a vector of the disclosure when not used in combination with a contrast agent. In various embodiments, the transduction of cells is increased by at least about 1%, or at least about 5%, at least about 10%, at least about 20%, at least about 30%, at least about 40%, at least about 50%, at least about 60%, at least about 70%, at least about 80%, at least about 90%, at least about 100%, at least about 120%, at least about 150%, at least about 180%, at least about 200%, at least about 250%, at least about 300%, at least about 350%, at least about 400%, at least about 450%, at least about 500% or more when a vector of the disclosure is used in combination with a contrast agent as described herein, relative to the transduction of a vector of the disclosure when not used in combination with a contrast agent. In further embodiments, the transduction of cells is increased by about 10% to about 50%, or by about 10% to about 100%, or by about 5% to about 10%, or by about 5% to about 50%, or by about 1% to about 500%, or by about 10% to about 200%, or by about 10% to about 300%, or by about 10% to about 400%, or by about 100% to about 500%, or by about 150% to about 300%, or by about 200% to about 500% when a vector of the disclosure is used in combination with a contrast agent as described herein, relative to the transduction of a vector of the disclosure when not used in combination with a contrast agent.

In some aspects, it is contemplated that the transduction of cells is further increased when a vector of the disclosure is used in combination with a contrast agent and when the patient is put in the Trendelenberg position (head down position). In some embodiments, for example, the patients is tilted in the head down position at about 1 degree to about 30 degrees, about 15 to about 30 degrees, about 30 to about 60 degrees, about 60 to about 90 degrees, or about 90 up to about 180 degrees) during or after intrathecal vector infusion. In various embodiments, the transduction of cells is increased by at least about 1%, or at least about 5%, at least about 10%, at least about 20%, at least about 30%, at least about 40%, at least about 50%, at least about 60%, at least about 70%, at least about 80%, at least about 90%, at least about 100%, at least about 120%, at least about 150%, at least about 180%, at least about 200%, at least about 250%, at least about 300%, at least about 350%, at least about 400%, at least about 450%, at least about 500% or more when a vector of the disclosure is used in combination with a contrast agent and Trendelenberg position as described herein, relative to the transduction of a vector of the disclosure when not used in combination with a contrast agent and Trendelenberg position. In further embodiments, the transduction of cells is increased by about 10% to about 50%, or by about 10% to about 100%, or by about 5% to about 10%, or by about 5% to about 50%, or by about 1% to about 500%, or by about 10% to about 200%, or by about 10% to about 300%, or by about 10% to about 400%, or by about 100% to about 500%, or by about 150% to about 300%, or by about 200% to about 500% when a vector of the disclosure is used in combination with a contrast agent and Trendelenberg position as described herein, relative to the transduction of a vector of the disclosure when not used in combination with a contrast agent and Trendelenberg position.

The disclosure also provides aspects wherein intrathecal administration of a vector of the disclosure and a contrast agent to the central nervous system of a patient in need thereof results in an increase in survival of the patient relative to survival of the patient when a vector of the disclosure is administered in the absence of the contrast agent. In various embodiments, administration of a vector of the disclosure and a contrast agent to the central nervous system of a patient in need thereof results in an increase of survival of the patient of at least about 1%, at least about 5%, at least about 10%, at least about 20%, at least about 30%, at least about 40%, at least about 50%, at least about 60%, at least about 70%, at least about 80%, at least about 90%, at least about 100%, at least about 150%, at least about 200% or more relative to survival of the patient when a vector of the disclosure is administered in the absence of the contrast agent.

The disclosure also provides aspects wherein intrathecal administration of a vector of the disclosure and a contrast agent to the central nervous system of a patient in need thereof put in the Trendelenberg position results in a further increase in survival of the patient relative to survival of the patient when a vector of the disclosure is administered in the absence of the contrast agent and the Trendelenberg position. In various embodiments, administration of a vector of the disclosure and a contrast agent to the central nervous system of a patient in need thereof put in the Trendelberg position results in an increase of survival of the patient of at least about 1%, at least about 5%, at least about 10%, at least about 20%, at least about 30%, at least about 40%, at least about 50%, at least about 60%, at least about 70%, at least about 80%, at least about 90%, at least about 100%, at least about 150%, at least about 200% or more relative to survival of the patient when a vector of the disclosure is administered in the absence of the contrast agent and the Trendelenberg position.

It will be understood by one of ordinary skill in the art that a polynucleotide delivered using the materials and methods of the invention can be placed under regulatory control using systems known in the art. By way of non-limiting example, it is understood that systems such as the tetracycline (TET on/off) system [see, for example, Urlinger et al., *Proc. Natl. Acad. Sci. USA* 97(14):7963-7968 (2000) for recent improvements to the TET system] and Ecdysone receptor regulatable system [Palli et al., *Eur J. Biochem* 270: 1308-1315 (2003] may be utilized to provide inducible polynucleotide expression. It will also be understood by the skilled artisan that combinations of any of the methods and materials contemplated herein may be used for treating a neurodegenerative disease.

The present invention is illustrated by the following examples, wherein Example 1 describes the production of an exemplary rAAV9, Example 2 describes the intrathecal administration of rAAV9, Example 3 describes the increase in survival of SMN mutant mice following intracerebroventricular (ICV) injection of rAAV9 SMN with contrast agent and Example 4 describes motor neuron transduction with a rAAV9 in cynomolgus monkeys.

Example 1

The ability of rAAV9 to target and express protein in the central nervous system was evaluated in an in vivo model system. The rAAV genome included in sequence an AAV2 ITR, the chicken β-actin promoter with a cytomegalovirus enhancer, an SV40 intron, green fluorescent protein (GFP) DNA, a polyadenylation signal sequence from bovine growth hormone and another AAV2 ITR, as previously described in Bevan et al., *Molecular Therapy*, 19(11): 1971-1980 (2011).

Self-complementary AAV9 (AAV9 GFP) was produced by transient transfection procedures using a double-stranded AAV2-ITR-based CB-GFP vector, with a plasmid encoding Rep2Cap9 sequence as previously described [Gao et al., *J. Virol.*, 78: 6381-6388 (2004)] along with an adenoviral helper plasmid pHelper (Stratagene, Santa Clara, Calif.) in 293 cells. The serotype 9 sequence was verified by sequencing and was identical to that previously described. Virus was produced in three separate batches for the experiments and purified by two cesium chloride density gradient purification steps, dialyzed against PBS and formulated with 0.001% Pluronic-F68 to prevent virus aggregation and stored at 4° C. All vector preparations were titered by quantitative PCR using Taq-Man technology. Purity of vectors was assessed by 4-12% sodium dodecyl sulfate-acrylamide gel electrophoresis and silver staining (Invitrogen, Carlsbad, Calif.).

Example 2

Although some neurological disorders are caused by defects in ubiquitously expressed proteins, in other disorders gene expression in the CNS alone may have a substantial impact. The invention contemplates that gene delivery to the CSF can produce transduction along the neuraxis with the added benefit of potentially lowering the required dose. Thus, to effect more localized CNS delivery, intrathecal and/or intracisternal injections of 5.2×10 12 vg/kg of AAV9 GFP and a non-ionic, low-osmolar contrast agent into 5-day-old pigs (n=3 each) were performed, and their brains and spinal cords were examined for GFP expression.

Intrathecal Injection. Farm-bred sows (*Sus scrofa domestica*) were obtained from a regional farm. Five-day-old (P5) piglets received 0.5 cc/kg ketamine induction anesthesia and then were maintained by mask inhalation of 5% isoflurane in oxygen. Body temperature, electrocardiogram, and respiratory rate were monitored throughout the procedure. For lumbar puncture, piglets were placed prone and the spine was flexed in order to widen the intervertebral spaces. The anterior-superior iliac spines were palpated and a line connecting the two points was visualized. The intervertebral space rostral to this line is ~L5-L6. Intraoperative fluoroscopy confirmed rostral-caudal and mediolateral trajectories. Using sterile technique, a 25-gauge needle attached to a 1-ml syringe was inserted. Gentle negative pressure was applied to the syringe as the needle was passed until a clear flash of CSF was visualized. For cisterna puncture, the head of the piglet was flexed while maintaining the integrity of the airway. Fluoroscopy again confirmed adequate trajectory. A 25-gauge needle was passed immediately caudal to the occipital bone, and a flash of clear CSF confirmed entry into the cistern magna.

For vector or control delivery, the syringe was removed while the needle was held in place. A second 1-cc syringe containing either viral solution ($5.2 \times 10^{12}$ vg/kg) or PBS was secured and the solution was injected into the intrathecal space at a slow and constant rate. After delivery, ~0.25 ml of sterile PBS was flushed through the spinal needle so as to ensure full delivery of reagent. An iohexol radioopaque agent [Omnipaque™ (iohexol, N,N'-Bis(2,3-dihydroxypropyl)-5-[N(2,3-dihydroxypropyl)-acetamido]-2,4,6-trioldo-isophthalamide), GE Healthcare, Waukesha, Wis.] and recording intrathecal spread with real-time continuous fluoroscopy.

Perfusion and tissue-processing. All subjects were sacrificed between 21 and 24 days post-injection. Subjects were deeply anesthetized by intramuscular injection of Telazol followed by Propofol. A midventral sternal thoracotomy was performed and a cannula was inserted in the aorta through the left ventricle. The right atrium was opened and 0.5-1 l of PBS was injected through the cannula by gravity flow, followed by perfusion with 1 l of 4% paraformaldehyde in phosphate buffer (pH 7.4). Organs were removed and post-fixed 48 hours in 4% paraformaldehyde before further processing for histological sectioning or stored long-term in 0.1% NaN3 PBS solution.

Histology and microscopy. Spinal cord segments were embedded in 3% agarose before cutting into 40-μm horizontal sections using a Leica VT1200 vibrating microtome (Leica Microsystems, Buffalo Grove, Ill.). Sections were transferred in Tris-buffered saline and stored at 4° C. until processing. Brains were cryoprotected by successive incubation in 10, 20, and 30% sucrose solutions. Once sufficiently cryoprotected (having sunk in 30% sucrose solution), brains were frozen and whole-mounted on a modified Leica SM 2000R sliding microtome (Leica Microsystems) in OCT (Tissue-Tek, Torrance, Calif.) and cut into 40-μm coronal sections.

For immunofluorescent determination of cell types transduced, floating sections were submerged in blocking solution (10% donkey serum, 1% Triton-X100 in Tris-buffered saline) for 1 hour followed by overnight incubation in primary antibody solution at 4° C. The following primary antibodies were used in this study: Rabbit-anti-GFP (1:500; Invitrogen), goat-anti-ChAT (1:100; Millipore, Billerica, Mass.), guinea-pig-anti-GFAP (1:1,000; Advanced Immunochemical, Long Beach, Calif.) and rabbit-anti-Iba1 (1:500; Dako, *Carpentaria*, CA). Primary antibodies were detected using Fitc-, Cy3-, or Cy5-conjugated secondary antibodies (1:1,000; Jackson ImmunoResearch, West Grove, Pa.) and mounted in PVA-DABCO medium.

For immunohistochemical staining, sections were incubated at room temperature in 0.5% $H_2O_2$/10% MeOH solution and subsequently blocked and stained as above with rabbit-anti-GFP overnight. Anti-GFP antibodies were detected using biotinylated donkey-anti-rabbit secondary antibody (1:200; Jackson ImmunoResearch) and developed using Vector NovaRed per the provided protocol (Vector Labs, Burlingame, Calif.). Sections were then mounted in Cytoseal 60 medium (Thermo Fisher Scientific, Kalamazoo, Mich.).

Non-neural tissues were cut to ~1 cm3 blocks and cryoprotected by overnight incubation in 30% sucrose solution. They were then embedded in gum tragacanth and flash-frozen in liquid nitrogen-cooled isopentane. Samples were cut by cryostat into 10-12 μm sections and slides stored at −20° C. GFP expression was detected by a similar immunofluorescent protocol as above with the addition of DAPI in secondary antibody solution (1:1,000; Invitrogen).

Fluorescent images were captured using a Zeiss 710 Meta confocal microscope (Carl Zeiss MicroImaging, Thornwood, N.Y.) located at TRINCH and processed with LSM software.

Whole brain sections were scanned to ×40 resolution at the Biopathology Center in the Research Informatics Core at the Research Institute at Nationwide Children's Hospital using an Aperio automated slide scanner (Aperio, Vista, Calif.) and resulting images were processed with ImageScope software.

In all animals, GFP expression was seen in the dorsal root ganglia as well as the spinal cord gray and white matter. Importantly, AAV9 GFP injection into either the cisternal space at the base of the skull or the intrathecal space at L5 resulted in extensive motor neuron transduction and glia at all levels of the spinal cord as examined by in situ hybridization. Large ventral horn neurons were also positive for GFP expression by immunohistochemistry at all levels of spinal cord. Immunofluorescence confirmed that the GFP+ cells expressed the motor neuron marker ChAT.

Finally, to further characterize the pattern of expression following cisternal or intrathecal injection of AAV9-GFP into 5-day-old pigs, brains were examined for transgene expression again using GFP immunofluorescence The regions with the highest levels of GFP expression were cerebellar Purkinje cells, nerve fibers within the medulla as well as discrete nuclei, such as the olivary nucleus. Expression within the rest of the brain was restricted to scattered cells near the meningeal surfaces. Examination of GFP expression in peripheral organs yielded no visible GFP expression indicating that the majority of the virus was localized to the CNS.

Thus, AAV9 injection into the cerebral spinal fluid of young pigs efficiently targeted motor neurons.

Example 3

The effects of in vivo delivery of rAAV9 SMN [see Foust et al., *Nature Biotechnology* 28(3): 271-274 (2010) and description hereinabove, wherein the sequence of the vector genome insert is shown as nucleotides 980-3336 of SEQ ID NO: 1] and contrast agent to the cerebral spinal fluid (CSF) of SMN mutant mice was tested.

Briefly, the rAAV9 SMN was mixed with contrast agent, followed by ICV injection to effect placement of the composition to the CSF of SMN mutant mice. As a control experiment, the rAAV9 SMN vector was injected without contrast agent into a separate group of SMN mutant mice.

Results showed that injection of rAAV9 SMN at ~$10^8$ vg/kg with contrast agent yielded a median survival of SMN mutant mice of 20 days, while injection of an equivalent amount of rAAV9 SMN in the absence of contrast agent yielded no survival.

Injection of rAAV9 SMN at ~$10^9$ vg/kg with contrast agent yielded a median survival of SMN mutant mice of over 70 days, versus no survival of SMN mutant mice that were injected with an equivalent amount of rAAV9 SMN in the absence of contrast agent.

Finally, injection of rAAV9 SMN at ~$10^{10}$ vg/kg with contrast agent yielded a median survival of SMN mutant mice of over 100 days, versus a median survival of 70 days in SMN mutant mice that were injected with an equivalent amount of rAAV9 SMN in the absence of contrast agent.

Thus, the survival of SMN mutant mice is increased following injection of rAAV9 SMN with contrast agent, relative to the survival of SMN mutant mice following injection of rAAV9 SMN in the absence of contrast agent.

Example 4

Three one year old cynomolgus monkeys received intrathecal injections of $1 \times 10^{13}$ vg/Kg rAAV9 encoding a shRNA and GFP. The injection was performed by lumbar puncture into the subarachnoid space of the lumbar thecal sac. The rAAV9 was resuspended with omnipaque (iohexol), an iodinated compound routinely used in the clinical setting. Iohexol is used to validate successful subarachnoid space cannulation and was administered at a dose of 100 mg/Kg. The subject was placed in the lateral decubitus position and the posterior midline injection site at ~L4/5 level identified (below the conus of the spinal cord). Under sterile conditions, a spinal needle with stylet was inserted and subarachnoid cannulation was confirmed with the flow of clear CSF from the needle. In order to decrease the pressure in the subarachnoid space, 0.8 ml of CSF was drained, immediately followed by injection with a mixture containing 0.7 mL iohexol (300 mg/ml formulation) mixed with 2.1 mL of virus (2.8 ml total). To investigate if rostral flow distribution of the virus could improve cell transduction in the cervical area, one subject was let recover in the lateral decubitus position, and the second and third subjects were tilted in the Trendelenberg position (head down position). This is a routine procedure when performing CT myelograms in human subjects.

Cynomolgus monkeys injected with virus were euthanized 2 weeks post injection. Animals were anesthetized with sodium pentobarbital at the dose of 80-100 mg/kg intravenously and perfused with saline solution. Brain and spinal cord dissection were performed immediately and tissues were processed either for nucleic acid isolation (snap frozen) or post-fixed in 4% paraformaldehyde and subsequently cryoprotected with 30% sucrose and frozen in isopentane at $-65°$ C. 12 µm coronal sections were collected from lumbar cord using a cryostat for free floating immunostaining with green fluorescent protein (GFP) to identify the cells transduced by the virus and choline acetyl transferase (Chat) to identify the motor neurons. Double positive cells were counted in 10 sections of cervical, thoracic and lumbar cord and their number was normalized to the total number of Chat positive cells in the same segment.

The cell counts revealed that tilting the subjects after virus infusion results in a two-fold (100%) improvement in motor neuron transduction at the thoracic and cervical levels.

While the present invention has been described in terms of various embodiments and examples, it is understood that variations and improvements will occur to those skilled in the art. Therefore, only such limitations as appear in the claims should be placed on the invention.

All documents referred to herein are incorporated by reference in their entirety.

The invention claimed is:

1. A method of treating a lysosomal storage disorder associated with a mutation in the TPP1 gene in a patient in need thereof, the method comprising: intrathecally administering a) a recombinant AAV9 (rAAV9) comprising an rAAV9 genome comprising a neuronal ceroid lipofuscinosis 2 (CLN2) gene wherein the gene is operatively linked to an expression control sequence; and (b) a non-ionic, low-osmolar contrast agent, wherein the intrathecal administration of the composition results in delivery of the CLN2 gene to the central nervous system (CNS) of the patient.

2. The method of claim 1, wherein the non-ionic, low-osmolar contrast agent is selected from the group consisting of iobitridol, iohexol, iomeprol, iopamidol, iopentol, iopromide, ioversol, ioxilan, and combinations thereof.

3. The method of claim 1, wherein the non-ionic, low-osmolar contrast agent is iohexol.

4. The method of claim 1, wherein the rAAV9 genome is a single-stranded genome.

5. The method of claim 1, wherein the rAAV9 genome is a self-complementary genome.

6. A method of delivering CLN2 gene to CNS of a patient in need thereof, comprising intrathecally administering to the patient a composition comprising a) a rAAV9 comprising an rAAV9 genome comprising a CLN2 gene wherein the gene is operatively linked to an expression control sequence and (b) a non-ionic, low-osmolar contrast agent—wherein the intrathecal administration of the composition results in delivery of the CLN2 gene to the CNS of the patient.

7. The method of claim 6, wherein the non-ionic, low-osmolar contrast agent is selected from the group consisting of iobitridol, iohexol, iomeprol, iopamidol, iopentol, iopromide, ioversol, ioxilan, and combinations thereof.

8. The method of claim 6, wherein the non-ionic, low-osmolar contrast agent is iohexol.

9. The method of claim 6, wherein the rAAV9 genome is a single-stranded genome.

10. The method of claim 6, wherein the rAAV9 genome is a self-complementary genome.

* * * * *